United States Patent [19]

Taylor et al.

[11] Patent Number: 4,988,813

[45] Date of Patent: Jan. 29, 1991

[54] PROCESS FOR THE PREPARATION OF FUSED PYRIDINE COMPOUNDS

[75] Inventors: Edward C. Taylor, Princeton; George S. K. Wong, Fort Lee, both of N.J.

[73] Assignee: The Trustees of Princeton University, Princeton, N.J.

[21] Appl. No.: 229,694

[22] Filed: Aug. 8, 1988

Related U.S. Application Data

[62] Division of Ser. No. 922,511, Oct. 20, 1986, Pat. No. 4,818,819.

[51] Int. Cl.$^5$ ............................................. C07D 471/04
[52] U.S. Cl. .................................... 544/279; 544/257; 546/350
[58] Field of Search ................. 544/279, 257; 546/350

[56] References Cited

PUBLICATIONS

Sakamoto et al., "A Facile Synthesis of Ethynyl-Substituted Six-Membered N-Heteroaromatic Compounds", Synthesis, 1983. p. 312.

Edo et al., Chem. Abstr. 91: 20435c.

Primary Examiner—Mukund J. Shah
Assistant Examiner—C. L. Cseh
Attorney, Agent, or Firm—Mathews, Woodbridge & Collins

[57] ABSTRACT

2-Amino-4-hydroxy-6-[2-(4-carboxyphenyl)alk-1-en-1-yl]pyrido[2,3,-d]pyrimidines and 2-amino-4-hydroxy-6-[2-(4-carboxyphenyl)alk-1-yn-1-yl]pyrido[2,3-d]pyrimidines are prepared through through the reaction of a haloaromatic compound and an unsaturated compound in the presence of a palladium catalyst. The products are chemical intermediates for the preparation of antineoplastic agents.

A typical embodiment is the reaction of a protected 2-amino-4-hydroxy-6-ethynylpyrido[2,3-d]pyrimidine and an ester of 4-iodobenzoic acid.

19 Claims, No Drawings

PROCESS FOR THE PREPARATION OF FUSED PYRIDINE COMPOUNDS

CROSS REFERENCE

This is a divisional of Ser. No. 922,511 filed Oct. 20, 1986, now U.S. Pat. No. 4,818,819, issued Apr. 4, 1989.

BACKGROUND OF THE INVENTION

This invention pertains to a process for the preparation of known therapeutic agents and to chemical intermediates useful therein.

Compounds of the formula:

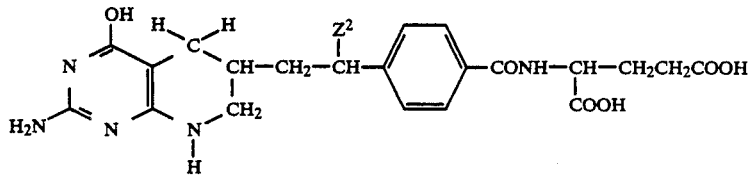

in which $Z^2$ is hydrogen, methyl, or ethyl are broad spectrum antineoplastic agents, see published PCT Application No. WO 86/05181 and corresponding U.S. Pat. No. 4,684,653. N-(4-[2-(2-amino-4-hydroxy-5,6,7,8-tetrahydropyrido[2,3-d]pyrimidin-6-yl)ethyl]benzoyl)-L-glutamic acid, which is representative, has been prepared previously through an eighteen step synthesis in which a 2-(protected amino)-4-hydroxy-6-[2-(4-carboxyphenyl)ethenyl]pyrido[2,3-d]pyrimidine is coupled with a diester of L-glutamic acid utilizing peptide condensation techniques. The resultant dialkyl N-(4-[2-(2-protected amino-4-hydroxypyrido[2,3-d]pyrimidin-6-yl)ethenyl]benzoyl)-L-glutamate is then hydrogenated, following which the protecting groups are removed [see Taylor et al., *J. Med. Chem.* 28:7, 914 (1985)].

DETAILED DESCRIPTION

The present invention involves a simplified process for the preparation of important intermediates useful in the synthesis of the foregoing compounds; in particular, intermediates of the formula:

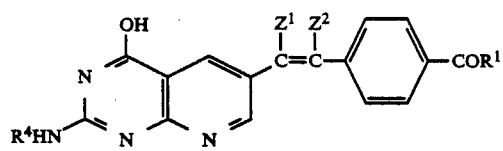

(I)

wherein
$R^1$ is $NHCH(COOR^2)CH_2CH_2COOR^2$ or $OR^2$;
$R^2$ is hydrogen or a carboxylic acid protecting group;
$R^4$ is hydrogen or an amino protecting group;
$Z^1$ when taken independently of $Z^2$ is hydrogen; and
$Z^2$ when taken independently of $Z^1$ is hydrogen, methyl or ethyl; or
$Z^1$ and $Z^2$ when taken together are a carbon-carbon bond.

A number of compounds falling within Formula I in which $Z^1$ is hydrogen and $Z^2$ is hydrogen, methyl or ethyl are known from PCT Application No. WO 86/05181; others wherein $Z^1$ and $Z^2$ are a carbon-carbon bond are novel and constitute part of the present invention.

The process involves the step of allowing an unsaturated compound (as hereinafter defined) to react with a haloaromatic compound (as also hereinafter defined) in the presence of a palladium catalyst. The reaction has a number of different embodiments but each of these has in common the use of an organopalladium reactant which is generated from a palladium complex and the haloaromatic compound and which reacts with the unsaturated compound.

The palladium complexes are those which have been employed previously in the reaction of aryl halides and allylic alcohols, as described for example by Melpoler et al., *J. Org. Chem.*, 41, No. 2, 1976, 265; Chalk et al., *J. Org. Chem.*, 41, No. 7, 1976, 1206; Arai et al., *J. Heterocyclic Chem.*, 15, 351 (1978); Tamuru et al., *Tetrahedron Papers*, 10, 919 (1978) 919; *Tetrahedron*, 35, 329 (1979). Particularly useful are the palladium/trisubstituted-phosphine complexes of Sakamoto, *Synthesis*, 1983, 312; e.g., a trisubstituted-phosphine such as a triarylphosphine, as for example triphenylphosphine, or a trialkylphosphine; a palladium salt such as palladium acetate or a palladium halide such as palladium chloride; and a cuprous halide, such as cuprous iodide.

The reaction preferably is conducted in the presence of at least one molar equivalent of a secondary or tertiary amine which acts as an acid acceptor, as for example triethylamine, or diethylamine, and under an inert atmosphere, optionally in the presence of an inert polar solvent such as acetonitrile, dimethylformamide, N-methylpyrrolidone and the like. Particularly preferred is the use of acetonitrile which serves as a solvent not only for the reactants but also for the salt formed from the acid acceptor and acid generated. Moderately elevated temperatures, as for example from about 75° to 125° C., preferable at or below 100° C., generally are advantageous.

The following four embodiments utilize the foregoing palladium catalysts and differ in the nature of haloaromatic compound and unsaturated compound employed as the reactants. Haloaromatic compounds as herein used include halopyridines, fused halopyridines and halobenzoic acid derivatives. The unsaturated compound includes both alkenes and alkynes as well as pyridines, fused pyridines and benzoic acid derivatives substituted with an alkenyl or alkynyl group.

In a first embodiment, the haloaromatic compound is a pyridine of the formula:

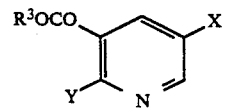

(II)

wherein
Y is amino or a nucleofuge;
X is bromo or iodo; and
$R^3$ is alkyl of 1 to 4 carbon atoms.

The haloaromatic compound of Formula II is allowed to react with an unsaturated compound of the formula:

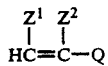  (III)

wherein $Z^1$ when taken independently of $Z^2$ is hydrogen;

$Z^2$ when taken independently of $Z^1$ is hydrogen, methyl or ethyl; or $Z^1$ and $Z^2$ when taken together are a carbon-carbon bond, and Q is a trisubstituted silyl group or a benzoyl group of the formula:

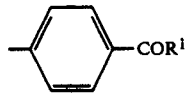

wherein $R^1$ is $-NHCH(COOR^2)CH_2CH_2COOR^2$ or $OR^2$; and $R^2$ is a carboxylic acid protecting group.

In a second embodiment, the haloaromatic compound is a fused pyridine of the formula:

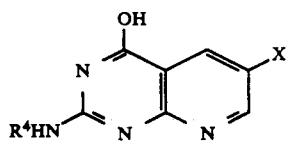  (IV)

wherein $R^4$ is hydrogen or an amino protecting group and

X is bromo or iodo.

A compound of Formula IV is allowed to react with an unsaturated compound of Formula III, discussed above, in the presence of the palladium catalyst.

In a third embodiment, the haloaromatic compound is of the formula:

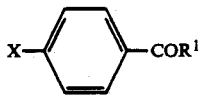  (V)

wherein

X is bromo or iodo;

$R^1$ is $-NH-CH(COOR_2)CH_2CH_2COOR^2$ or $OR^2$; and $R^2$ is a carboxylic acid protecting group;

and the unsaturated compound is a pyridine of the formula:

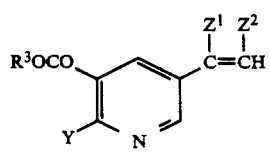  (VI)

wherein

Y is amino or a nucleofuge;

$Z^1$ when taken independently of $Z^2$ is hydrogen;

$Z^2$ when taken independently of $Z^1$ is hydrogen, methyl or ethyl; or $Z^1$ and $Z^2$ when taken together are a carbon-carbon bond; and $R^3$ is alkyl of 1 to 4 carbon atoms.

In a fourth embodiment, a haloaromatic compound of Formula V above is allowed to react with a pyrido[2,3-d]pyrimidine of the formula:

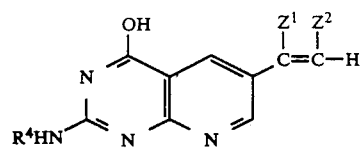  (VII)

wherein $R^4$ is hydrogen or an amino protecting group;

$Z^1$ when taken independently of $Z^2$ is hydrogen; and $Z^2$ when taken independently of $Z^1$ is hydrogen, methyl or ethyl; or $Z^1$ and $Z^2$ when taken together are a carbon-carbon bond.

In the first embodiment set forth above when Q is the depicted 4-carboxyphenyl group, and in the third embodiment, there is produced a novel intermediate of the formula:

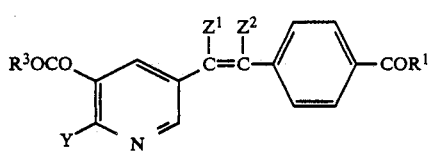  (VIII)

When allowed to react with guanidine the intermediates of Formula VIII are converted directly to a 2-amino-4-hydroxy-6-substituted-pyrido[2,3-d]pyrimidine of Formula I in which $R^4$ is hydrogen.

In the second and fourth embodiments, a compound of Formula I is formed directly.

In the above reactions, $R^2$ preferably is an alkyl group such as methyl, ethyl, sec.-butyl, t-butyl, or another known carboxylic acid protecting group such as nitrobenzyl, 4-methoxybenzyl, diphenylmethyl, trichloroethyl, 1-ethoxyethyl, 1-ethylthioethyl, and the like. When $R^1$ is the depicted glutamic acid residue (which will be of L-configuration), typically the compound will be a L-glutamic acid dialkylester such as the dimethyl, diethyl, or di-(tert.-butyl) ester.

The compounds of Formula II can be prepared by esterification of the known 1,2-dihydro-2-oxo-3-pyridine carboxylic acid, introduction of a 5-iodo or 5-bromo group through treatment with N-iodosuccinimide or N-bromosuccinimide to yield the 5-iodo- or 5-bromo-2-oxo-1,2-dihydro-3-pyridine carboxylate, respectively, and replacement of the 2-oxo group with a suitable nucleofuge; e.g., chlorination with phosphorus oxychloride. The term "nucleofuge" refers to a conventional leaving group which is replaced by nucleophilic reagents. [See *Organic Chemistry*, Morrison and Boyd, Allyn and Breur, 4th Edition, p 205]. Typical nucleofuges thus include chloro, bromo, iodo, an aryl or alkylsulfinyl or sulfonyl group of up to 10 carbon atoms, an arylthio or alkylthio group of up to 10 carbon atoms, mercapto, and alkoxy of up to 10 carbon atoms. Preferably Y is chloro. X may be bromo or iodo; iodo is preferred.

Compounds of Formula IV can be prepared through the condensation of 2,4-diamino-6-hydroxy-pyrimidine and a halomalonaldehyde, such as bromomalonaldehyde or iodomalonaldehyde, preferably bromomalonaldehyde.

Alternatively, compounds of Formula IV can be obtained from a pyridine of Formula II through treatment with guanidine in a manner analogous to that described above, followed by optional protection of the amino group, as for example by acylation.

Compounds of Formula VI and VII can be prepared from starting materials of Formulas II and IV, respectively, by utilization of an unsaturated compound of Formula III in which Q is a trisubstituted silyl protecting group, followed by hydrolysis of the silyl group.

The amino and carboxylic acid protecting groups discussed herein are those conventionally employed, as described for example by Greene in "Protective Groups in Organic Synthesis", John Wiley & Sons, Inc., 1981, and McOmie in "Protective Groups in Organic Chemistry", Plenum Press, 1983. Particularly preferred $R^4$ protecting groups are alkanoyl groups such as acetyl, propionyl, pivaloyl, and the like.

Catalytic hydrogenation of a compound of Formula I yields the corresponding 2-amino(or 2-protected amino)-4-hydroxy-6-substituted-5,6,7,8-tetrahydropyrido[2,3-d]pyrimidine of the formula:

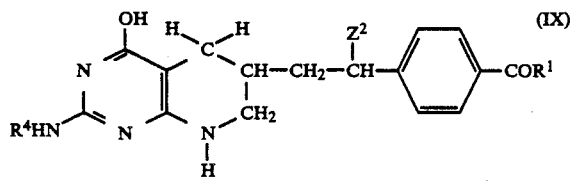

in which $R^4$ is hydrogen or an amino protecting group and $R^1$ and $Z^2$ are as defined above.

When in the compounds of Formula IX $R^1$ is —NH(COOR$^2$)CH$_2$CH$_2$COOR$^2$ and $Z^2$ is hydrogen, the resulting product is a protected derivative of the known [N-(4-[2-(2-amino-4-hydroxy-5,6,7,8-tetrahydropyrido[2,3-d]pyrimidin-6-yl)ethyl]benzoyl)-L-glutamic acid; e.g., diethyl N-(4-[2-(2-amino-4-hydroxy-5,6,7,8-tetrahydropyrido[2,3-d]pyrimidin-6-yl)ethyl]-benzoyl)-L-glutamate (or the protected amino derivative thereof), which then is subjected to hydrolysis or hydrogenolysis as previously described to remove the protecting groups and yield the known N-(4-[2-(2-amino-4-hydroxy-5,6,7,8-tetrahydropyrido[2,3-d]pyrimidin-6-yl)ethyl]benzoyl)-L-glutamic acid.

Alternatively, if in the compounds of Formula IX, $R^1$ is —OR$^2$ in which $R^2$ is a carboxylic acid protecting group, the protecting group is removed in a known fashion, as for example hydrolysis with hydrogen chloride in nitromethane, to yield a 2-amino-4-hydroxy-5,6,7,8-tetrahydro-6-[2-(4-carboxyphenyl)ethyl]-pyrido[2,3-d]pyrimidine of the formula:

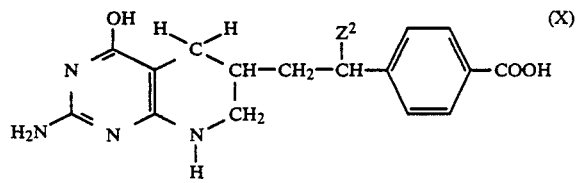

Following protection of the 2-amino group, as for example conversion to the N-pivaloyl derivative, a compound of Formula IX in which $R^1$ is OH is then coupled with a protected glutamic acid derivative in the manner described in PCT application No. WO 86/05181. The coupling reaction utilizes conventional condensation techniques for forming peptide bonds, such as activation of the carboxylic acid through formation of the mixed anhydride, treatment with DCC, or use of diphenylchlorophosphonate.

The hydrogenation of a compound of Formula I to a compound of Formula IX or Formula X generates a chiral center at the 6-position of the 5,6,7,8-tetrahydropyrido[2,3-d]pyrimidine ring. If $Z^2$ is other than hydrogen, a second chiral center is generated in the course of hydrogenation. In one embodiment of the present invention, the group $R^1$ in Formula I itself contains a chiral center and is in one of its chiral forms substantially free of the other. Thus $R^1$ can be the depicted L-glutamic acid group which itself is chiral. Alternatively, $R^2$ in the group —OR$^2$ in formula I is one enantiomeric form of a chiral group such as sec.-butyl, 2-methylbut-1-yl, 1-phenylethyl, (1R,2S)-(—)-ephedrine, 1-hydroxyprop-2-yl, 1-ethoxyethyl, 1-ethylthioethyl, the residue of a chiral terpene alcohol such as (1S,2R,5R)-(+)-isomenthol, (1R,2R,3R,5S)-(—)-isopinocampheol, (S)-perillyl alcohol, [(1S)-endo]-(—)-borneol, and the like. Use of a single chiral form of the protecting group $R^2$ yields a mixture of two diastereomers upon hydrogenation of a compound of Formula I in which $Z^2$ is hydrogen:

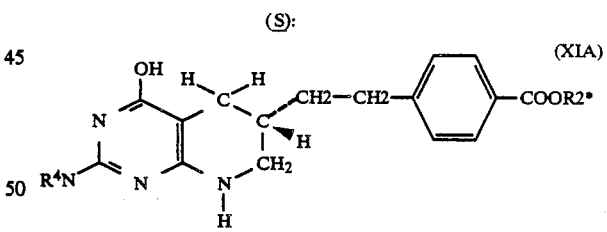

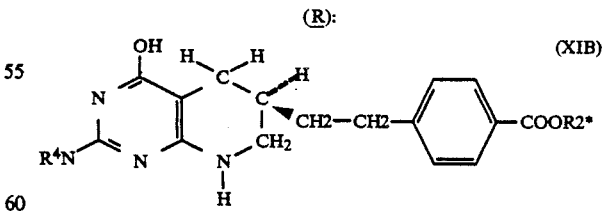

where $R^2*$ is a chiral form of $R^2$ substantially free of its enantiomer. The product of the hydrogenation is a mixture of two diastereomers which can be directly separated by taking advantage of their different solubility properties, thus eliminating the need for an independent separation step, as for example formation of a salt with a chiral acid.

Analogously if $Z^2$ is methyl or ethyl, use of a chiral $R^{2*}$ group produces a mixture of four diastereomers, e.g., $(R,R,R^{2*})$, $(R,S,R^{2*})$, $(S,S,R^{2*})$ and $(S,R,R^{2*})$ which are similarly separated.

The residue of the chiral alcohol is then hydrolytically removed from the individual separated diastereomers and which in the form of the free carboxylic acid is then coupled with a protected glutamic acid derivative as previously discussed.

The following examples will serve to further typify the nature of this invention but the invention should not be construed as being limited to these embodiments.

EXAMPLE 1

Methyl 2-chloro-5-iodo-3-pyridinecarboxylate

A. Methyl 2-Oxo-1,2-dihydro-3-pyridinecarboxylate

A mixture containing 27.8 g of 1,2-dihydro-2-oxo-3-pyridinecarboxylic acid, 3.0 ml of concentrated sulfuric acid in 500 ml of methanol, and 300 ml of benzene are heated under reflux for 2.5 hours. A Dean-Stark trap is then attached, and the azeotrope collected is removed periodically in 25 ml fractions over a period of 28 hours. The remaining solvent is removed by evaporation under reduced pressure and the solid residue suspended in 500 ml of cold water. The suspension is filtered (from which unreacted starting material can be recovered) and the filtrate continuously extracted with methylene chloride. The extracts are concentrated under reduced pressure to yield the title compound as a white solid which, upon recrystallization from 1.4 L of benzene, yields 19.48 g (64%) of methyl 2-oxo-1,2-dihydro-3-pyridinecarboxylate: m.p. 148°–151° C.; NMR (DMSO-$d_6$, 80 MHz) delta 3.72 (s, 3H), 6.25 (dd, 1H, J=7.1 Hz, J=6.3 Hz), 7.64 (dd, 1H, J=6.3 Hz, J=2.2 Hz), 8.03 (dd, 1H, J=7.1 Hz, J=2.2 Hz).

Ethyl 2-oxo-1,2-dihydro-3-pyridinecarboxylate is obtained in an analogous fashion utilizing ethanol in place of methanol.

B. Methyl 5-Iodo-2-oxo-1,2-dihydro-3-pyridinecarboxylate

A solution containing 19.48 g of methyl 2-oxo-1,2-dihydro-3-pyridinecarboxylate and 36.15 g of N-iodosuccinimide in 500 ml of anhydrous methylene chloride is heated at reflux under a nitrogen atmosphere in the dark for 48 hours. The reaction mixture is concentrated to 150 ml under reduced pressure and the solid which forms is collected by filtration and washed with small portions of cold methylene chloride and benzene to give 16.59 g (47%) of methyl 5-iodo-2-oxo-1,2-dihydro-3-pyridinecarboxylate as a pale yellowish solid. This material is sufficiently pure for the next reaction; its properties upon recrystallization from ethyl acetate are as follows: m.p. 190°–192° C.; NMR (DMSO-$d_6$, 300 MHz) delta 3.71 (s, 3H), 7.93 (d, 1H, J=2.26 Hz), 8.10 (d, 1H, J=2.26 Hz), IR (KBr) 2500–3050 (broad), 1725, 1630, 1585, 1475, 1425, 1320, 1260, 1235, 1180, 1150, 1105, 1065, 965, 875 and 800 cm$^{-1}$; M/S (279, M+), 247, 127 and 93. Anal. Calcd. for $C_7H_6INO_3$: C, 30.13; H, 2.17; I, 45.48; N, 5.02. Found: C, 30.24; H, 2.22; I, 45.55; N, 4.87. The filtrate is evaporated and the residue dissolved in 500 ml of methylene chloride. The organic solution is extracted with a 10% sodium thiosulfate solution, washed with a saturated sodium chloride solution, and dried over anhydrous sodium sulfate. The solution is concentrated under reduced pressure and the residue triturated with ethyl acetate and filtered to yield an additional 5.49 g (15%) of methyl 5-iodo-2-oxo-1,2-dihydro-3-pyridinecarboxylate.

Utilization of an equivalent amount of N-bromosuccinimide yields the corresponding methyl 5-bromo-2-oxo-1,2-dihydropyridine-3-carboxylate. m.p. 181°–182° C.; NMR (DMSO-$d_6$, 300 MHz) delta 3.72 (s, 3H), 7.97 (d, 1H, J=2.80 Hz), 8.05 (d, 1H, J=2.80 Hz); IR (KBr) 2500–3200 (broad), 1735, 1700, 1665, 1595, 1545, 1480, 1440, 1370, 1190, 1160, 1120, 970, 900, and 800 cm$^{-1}$.

C. Methyl 2-Chloro-5-Iodo-3-pyridinecarboxylate

Procedure 1:

To a mixture containing 2.0 g of methyl 5-iodo-1,2-dihydro-3-pyridinecarboxylate, 1.6 g of diethylaniline, 1.64 g of benzyltriethylammonium chloride and 3.6 ml of distilled phosphorus oxychloride in 100 ml of dry acetonitrile are added 15 drops of water. The mixture is heated under reflux for 18 hours. After cooling the reaction mixture to room temperature, the solvent is removed under reduced pressure and the residue taken up in methylene chloride and extracted with water. The organic solution is dried over anhydrous sodium sulfate and concentrated under reduced pressure. The residue is chromatographed on a column of flash silica gel using methylene chloride as the eluent. Evaporation of the eluent yields a pale yellowish solid which is recrystallized from aqueous ethanol to give 1.1 g (52%) of methyl 2-chloro-5-iodo-3-pyridinecarboxylate as a white solid: m.p. 73°–73.5° C.; NMR (80 MHz, CDCl$_3$) delta 3.96 (s, 3H), 8.43 (d, 1H, J=2.3 Hz), 8.71 (d, 1H, J=2.3 Hz).

Procedure 2

To a solution containing 0.12 ml of dry dimethylformamide and 0.14 ml of distilled phosphorus oxychloride in 20 ml of anhydrous methylene chloride are added 0.28 g of methyl 5-iodo-1,2-dihydro-3-pyridinecarboxylate in one portion. The mixture is stirred at room temperature under a nitrogen atmosphere for 28 hours. Workup as described in Procedure 1 yields 0.13 g (43%) of recrystallized methyl 2-chloro-5-iodo-3-pyridinecarboxylate.

Analogously prepared is methyl 2-chloro-5-bromo-3-pyridinecarboxylate, m.p. 49°–50° C.; NMR (CDCl$_3$, 300 MHz) delta 3.99 (s, 3H), 8.32 (d, 1H, J=2.86 Hz), 8.60 (d, 1H, J=2.86 Hz). Ethyl 2-chloro-5-iodo-3-pyridinecarboxylate and ethyl 2-chloro-5-bromo-3-pyridinecarboxylate can be prepared in the same fashion.

EXAMPLE 2

A. tert.-Butyl 4-Ethynylbenzoate

To a mixture of 5.5 g of dry tert.-butanol and 7.08 g of dry pyridine is added a solution of 9.79 g of 4-bromobenzoyl chloride in 20 ml of anhydrous methylene chloride. The mixture is stirred under nitrogen for 2 days. The reaction mixture is then diluted with methylene chloride, and the organic solution extracted with water, dried over anhydrous sodium sulfate, and concentrated under reduced pressure. The residual oil is distilled under reduced pressure to give 8.9 g (70%) of tert.-butyl 4-bromobenzoate as a colorless oil: b.p. 91°–92° C./1.2 mm; NMR (CDCl$_3$, 80 MHz) delta 1.59 (s, 9H), 7.53 (d, 2H, J=8.7 Hz); IR (neat) 2970, 1710, 1585, 1475, 1390, 1290, 1160, 1110, 1070, 845 and 745 cm$^{-1}$. Anal. Calcd. for $C_{11}H_{13}BrO_2$: C, 51.38; H, 5.09; Br, 31.08. Found: C, 51.41; H, 5.36; Br, 30.38.

B. tert.-Butyl 4-Ethynylbenzoate

A mixture containing 1.31 g of tert.-butyl 4-bromobenzoate, 1.0 g of trimethylsilylacetylene, 10 mg of palladium acetate and 15.6 mg of triphenylphosphine in 15 ml of anhydrous triethylamine is heated in a sealed container at 100° C. for 16 hours. After cooling to room temperature, the reaction mixture is diluted with methylene chloride and extracted with water. The organic solution is dried over anhydrous sodium sulfate and the solvent removed under reduced pressure. The dark residue is chromatographed a column of flash silica gel using a 10% ethyl acetate-hexanes mixture as the eluent to give tert.-butyl 4-(trimethylsilylethynylbenzoate as a dark oil: NMR (CDCl$_3$, 300 MHz) delta 0.26 (s, 9H), 1.59 (s, 9H), 7.49 (d, 2H, J=8.23 Hz), 7.91 (d, 2H, J=8.23 Hz). This is dissolved in 20 ml of anhydrous methanol, and then treated with 0.1 g of anhydrous potassium carbonate. The mixture is allowed to stir at room temperature under nitrogen for 3 hours. The reaction mixture is diluted with methylene chloride, extracted with water, dried over anhydrous sodium sulfate, and concentrated under reduced pressure. The residue is distilled under reduced pressure (60°-70° C./0.1 mm to give 0.75 g (73% over 2 steps) of tert.-butyl 4-ethynylbenzoate as a white solid: m.p. 71.5°-72° C.; NMR (CDCl$_3$, 80 MHz) delta 1.62 (s, 9H), 3.23 (s, 1H), 7.55 (d, 2H, J=8.11 Hz), 7.96 (d, 2H, J=8.11 Hz); IR (KBr) 3240, 2970, 2100, 1700, 1600, 1450, 1365, 1300, 1250, 1160, 1115, 1015, 845 and 765 cm$^{-1}$; M/S 202 (M+), 187, 157, 146, 129, 101, 75 and 57. Anal. Calcd. for C$_{13}$H$_{14}$O$_2$: C, 77.20; H, 6.98 Found: C, 76.86; H, 6.79.

EXAMPLE 3

Methyl 5-(4-tert.-butoxycarbonylphenylethynyl)-2-chloro-3-pyridinecarboxylate To a solution containing 0.53 g of methyl 2-chloro-5-iodo-3-pyridinecarboxylate and 0.4 g of tert.-butyl 4-ethynylbenzoate in 30 ml of triethylamine is added 0.19 g of triphenylphosphine, 0.06 g of palladium chloride, and 0.03 g of cuprous iodide. The mixture is heated under reflux under a nitrogen atmosphere for 4 hours. The solvent is removed under reduced pressure and the residue is subjected to radial chromatography on silica gel using methylene chloride as the eluent. The major fraction isolated from the plate contained 0.43 g (65%) of methyl 5-(4-tert.-butoxycarbonylphenylethynyl)-2-chloro-3-pyridinecarboxylate as a pale yellowish oil which crystallized on standing. A small portion of this material is recrystallized from hexanes: m.p. 123°-124° C.; NMR (CDCl$_3$, 300 MHz) delta 1.63 (s, 9H), 4.00 (s, 3H), 7.61 (d, 2H, J=8.15 Hz), 8.02 (d, 2H, J=8.15 Hz), 8.33 (d, 1H, J=2.16 Hz), 8.67 (d, 1H, J=2.16 Hz); IR (KBr) 3050, 3000, 2970, 2210, 1730, 1700, 1600, 1530, 1420, 1360, 1325, 1285, 1255, 1220, 1160, 1060, 845 and 765 cm$^{-1}$; M/S 373 (M++2), 371 (M+), 315, 298, 282 and 256. Anal. Calcd. for C$_{20}$H$_{18}$ClNO$_4$: C, 64.60; H, 4.88; Cl, 9.53; N, 3.77. Found: C, 64.87; H, 4.88; N, 3.77; Cl, 9.58.

EXAMPLE 4

2-Amino-4-hydroxy-6-(4-tert.-butoxycarbonylphenylethynyl)pyrido[2,3-d]pyrimidine To a solution containing 0.11 g of sodium in 30 ml of anhydrous tert.-butanol is added 0.45 g of guanidine hydrochloride. After stirring the mixture at room temperature for 15 minutes, 0.35 g of methyl 5-(4-tert.-butoxycarbonylphenyl)ethynyl-2-chloro-3-pyridinecarboxylate is added in one portion. The mixture is heated under reflux under nitrogen for 4 hours, cooled, diluted with ethanol, and the solvent removed under reduced pressure. The residue is dissolved in water and filtered to remove a small amount of insoluble material. The filtrate is acidified with a 3N hydrochloric acid solution and the precipitate that forms is collected by filtration, washed with water, and dried under reduced pressure to give 0.15 g (44%) of 2-amino-4-hydroxy-6-(4-tert.-butoxycarbonylphenylethynyl)pyrido[2,3-d]pyrimidine as a pale yellowish solid: m.p. >260° C.; NMR (DMSO-d$_6$, 80 MHz) delta 1.55 (s, 9H), 7.71 (d, 2H, J=8.6 Hz), 7.96 (d, 2H, J=8.6 Hz), 8.36 (d, 1H, J=2.5 Hz), 8.73 (d, 1H, J=2.5 Hz).

EXAMPLE 5

2-Amino-4-hydroxy-6-[4-carboxyphenylethynyl)-pyrido[2,3-d]pyrimidine

Thirty-four milligrams of 2-amino-4-hydroxy-6-(4-tert.-butoxycarbonylphenylethynyl)pyrido[2,3-d]pyrimidine is added to 15 ml of nitromethane which has been saturated with hydrogen chloride gas at 0° C. The mixture is stirred for 1 hour. Anhydrous ether is added and the solid filtered to give 27.6 mg (62%) of 2-amino-4-hydroxy-6-(4-carboxyphenylethynyl)-pyrido[2,3-d]pyrimidine as a pale yellowish solid: m.p. >260° C.; NMR (DMSO-d$_6$, 80 MHz) delta 7.71 (d, 2H, J=8.4 Hz), 8.00 (d, 2H, J=8.4 Hz), 8.40 (d, 1H, J=2.3 Hz), 8.75 (d, 1H, J=2.3 Hz).

EXAMPLE 6

2-Pivaloylamino-4-hydroxy-6-bromodopyrido[2,3-d]pyrimidine

A mixture of 21.72 g of 2-amino-4-hydroxy-6-bromopyrido[2,3-d]pyrimidine in 75 ml of pivalic anhydride is heated under reflux under a nitrogen atmosphere for 3 hours. The dark reaction mixture is cooled and anhydrous ether is added. The solid which forms is collected by filtration and dissolved in methylene chloride and the solution is filtered through silica gel in a sintered funnel. The silica gel pad is extracted with a 1% methanol:methylene chloride mixture. Evaporation of the filtrate gave 13.58 g (46%) of 6-bromo-2-pivaloylamino-5-deaza-4(3H)-pteridone as a pale yellowish solid. This material is sufficiently pure for the next reaction. A small amount of the solid was recrystallized from benzene: m.p. 258°-260° C.; NMR (CDCl$_3$, 300 MHz) delta 1.36 (s, 9H), 8.33 (brs, 1H), 8.65 (d, 1H, J=2.65 Hz), 8.92 (d, 1H, J=2.65 Hz); IR (KBr) 3250, 3190, 3100, 1670, 1610, 1550, 1480, 1375, 1275, 1220, 1140, 1020, 950, and 815 cm$^{-1}$. Anal. Calcd. for C$_{12}$H$_{13}$BrN$_4$O$_2$: C, 44.32; H, 4.03; N, 17.33; Br, 24.58. Found: C, 44.56; H, 3.85; N, 17.30; Br, 24.38.

Similarly prepared from the corresponding iodo compound is 2-pivaloylamino-4-hydroxy-6-iodopyrido[2,3-d]pyrimidine in 54% yield; m.p. 272°-273° C. (CH$_3$CN); NMR (CDCl$_3$, 300 MHz) delta 1.36 (s, 9H), 8.29 (brs, 1H), 8.83 (d, 1H, J=2.32 Hz) 9.06 (d, 1H, J=2.32 Hz); IR (KBr) 3240, 3200, 3120, 2970, 1670, 1610, 1580, 1545, 1480, 1430, 1370, 1325, 1270, 1230, 1140, 1020, 950, 810, and 760 cm$^{-1}$.

Analogously, a mixture of 0.52 g of 2-amino-4-hydroxy-6-iodopyrdo[2,3-d]pyrimidine and 0.03 g of 4-dimethylaminopyridine in 10 ml of acetic anhydride is heated under reflux under nitrogen for 3 hours. After cooling the reaction mixture to room temperature, anhydrous ether is added, and the reaction mixture filtered to give 0.52 g (87%) of 2-acetamido-4-hydroxy-6-iodopyrido[2,3-d]pyrimidine as a tan colored solid: m.p. >280° C.; NMR (DMSO-d$_6$, 80 MHz) delta 2.18 (s, 3H), 8.67 (d, 1H, J=2.5 Hz), 9.02 (d, 1H, J=2.5 Hz); M/S 330 (M+), 315 and 288.

EXAMPLE 7

Diethyl N-(4-ethynylbenzoyl)-L-glutamate

To a solution of 0.55 g of 4-ethynylbenzoic acid (obtained from tert.-butyl 4-ethynylbenzoate in 84% yield by hydrolysis with trifluoroacetic acid) in 50 ml of anhydrous ether and 25 ml of anhydrous tetrahydrofuran is added 1.58 ml of triethylamine. This is followed by 1.00 g of phenyl N-phenylphosphoraminochloridate. After stirring the reaction mixture at room temperature under nitrogen for 0.5 hour, 0.90 g of diethyl L-glutamate is added in one portion. The mixture is allowed to stir for another 8 hrs. After a workup, the residue is subjected to column chromatography using a 1% methanol:methylene chloride mixture as the eluent. The major fraction isolated from the column contained 0.68 g (54%) of diethyl N-(ethynylbenzoyl)-L-glutamate as an oil which slowly solidified: NMR (CDCl$_3$, 300 MHz) delta 1.25 (t, 3H, J=6.9 Hz), 1.33 (t, 3H, J=6.9 Hz), 2.11–2.60 (m, 4H), 3.23 (s, 1H), 4.09 (q, 2H, J=6.9 Hz), 4.27 (l, 2H, J=6.9 Hz), 4.80 (m, 1H), 7.12 (d, 1H, J=7.2 Hz), 7.59 (d, 2H, J=8.4 Hz), 7.81 (d, 2H, J=8.4 Hz); IR (KBr) 3330, 3280, 2990, 1735, 1640, 1520, 1380, 1200, 1105, 1020, 855, and 770 cm$^{-1}$.

EXAMPLE 8

Diethyl N-[4-(2-pivaloylamino-4-hydroxypyrido[2,3-d]pyrimidin-6-ylethynyl)benzoyl]-L-glutamate A mixture of 2.0 g of 6-bromo-2-pivaloylamino-4-hydroxypyrido[2,3-d]pyrimidine, 2.1 g of diethyl N-(4-ethynylbenzoyl)-L-glutamate, 2.57 ml of triethylamine, 0.11 g of palladium chloride, 0.32 g of triphenylphosphine, and 0.05 g of cuprous chloride in 150 ml of acetonitrile is heated at reflux under nitrogen for 2.5 hours. The solid which forms upon first cooling to room temperature is collected by filtration, and washed with cold acetonitrile to yield 1.91 g of diethyl N-[4-(2-pivaloylamino-4-hydroxypyrido[2,3-d]pyrimidin-6-ylethynyl)benzoyl]-L-glutamate which is sufficiently pure for further processing. Chromatography on silica gel with 5% methanol:methylene chloride showing the following physical properties. m.p. >250° C.; NMR (CDCl$_3$, 300 MHz) delta 1.25 (t, 3H, J=7.20 Hz), 1.33 (t, 3H, J=7.20 Hz), 1.36 (s, 9H), 2.14–2.62 (m, 4H), 4.14 (q, 2H, J=7.20 Hz), 4.27 (q, 2H, J=7.20 Hz), 4.79–4.86 (m, 1H), 7.30 (d, 1H, J=8.40 Hz), 7.63 (d, 2H, J=8.25 Hz), 7.86 (d, 2H, J=8.25 Hz), 8.51 (brs, 1H), 8.64 (d, 1H, J=2.40 Hz), 8.97 (d, 1H, J=2.40 Hz), 12.2 (brs, 1H); IR (KBr) 3330, 3290, 2970, 1730, 1655, 1590, 1530, 1440, 1370, 1260, 1140, 1020, 965, 925, 850, 810, and 760 cm$^{-1}$; $^{13}$C-NMR (CDCl$_3$, 75 MHz) delta 14.3, 27.1, 27.2, 30.7, 40.6, 52.7, 61.1, 62.0, 87.61, 92.71, 115.1, 117.3, 125.9, 127.4, 127.5, 132.0, 133.9, 138.7, 149.6, 157.8, 158.6, 160.5, 166.4 172.1, 173.5, 180.8. Anal. Calcd. for C$_{30}$H$_{33}$N$_5$O$_7$: C, 62.60; H, 5.78; N, 12.35. Found: C, 44.56; H, 3.85; N, 17.30; Br, 24.38.

EXAMPLE 9

2-Pivaloylamino-4-hydroxy-6-ethynylpyrido[2,3-d]pyrimidine

To a solution of 1.47 g of 2-pivaloylamino-4-hydroxy-6-trimethylsilylethynylpyrido[2,3-d]pyrimidine in 100 ml of anhydrous tetrahydrofuran are added, under nitrogen and at 0° C., 4.75 ml of 1M tetrabutylammonium fluoride in tetrahydrofuran. After 5 minutes, the reaction mixture is allowed to warm to room temperature and then is stirred for 2 hours. The solvent is removed under reduced pressure and the residue passed through a small pad of silica gel eluting with a 1% methanol: methylene chloride solution. The filtrate is concentrated under reduced pressure, and the residue purified further by radial chromatography on silica gel. The major fraction isolated from the plate contained 1.20 g (100%) of 2-pivaloylamino-4-hydroxy-6-ethynyl-pyrido[2,3-d]pyrimidine as an off white solid: m.p. >250° C.; NMR (CDCl$_3$, 300 MHz) delta 1.36 (s, 9H), 3.31 (s, 1H), 8.39 (brs, 1H), 8.60 (d, 1H, J=1.99 Hz), 8.49 (d, 1H, J=1.99 Hz); IR (KBr) 3300, 3200, 2980, 1670, 1620, 1550, 1470, 1445, 1380, 1325, 1280, 1240, 1140, 1025, and 970 cm$^{-1}$.

2-Pivaloylamino-4-hydroxy-6-trimethylsilylethynyl-pyrido[2,3-d]pyrimidine is prepared in 81% yield from 2-pivaloylamino-2-hydroxy-6-bromopyrido[2,3-d]pyrimidine and trimethylsilylacetylene analogously to Example 2B. m.p. >250° C.; NMR (CDCl$_3$, 300 MHz) delta 0.29 (s, 9H), 1.35 (s, 9H), 8.36 (brs, 1H), 8.57 (d, 1H, J=2.45 Hz), 8.92 (d, 1H, J=2.45 Hz); IR (KBr) 3200, 2970, 2170, 1680, 1620, 1545, 1475, 1440, 1380, 1275, 1250, 1145, 930, and 845 cm$^{-1}$.

EXAMPLE 10

Diethyl N-(4-bromobenzoyl)-L-glutamate

To a mixture of 0.92 g of 4-bromobenzoyl chloride and 1.0 g of diethyl L-glutamate in 50 ml to dry methylene chloride is added 1.16 ml of triethylamine. The reaction mixture is stirred overnight under nitrogen. After a standard workup, the methylene chloride solution is concentrated under reduced pressure, and the residue recrystallized from hexanes to give 0.68 g (46%) of analytically pure diethyl N-(4-bromobenzoyl)-L-glutamate as a white solid: m.p. 82.5°–83.5° C.; NMR (CDCl$_3$, 300 MHz) delta 1.26 (t, 3H, J=6.9 Hz), 1.33 (t, 3H, J=6.9 Hz), 2.11–2.60 (m, 4H), 4.14 (q, 2H, J=6.9 Hz), 4.27 (q, 2H, J=6.9 Hz) 4.78 (m, 1H), 7.14 (d, 1H, J=7.2 Hz), 7.61 (d, 2H, J=8.4 Hz), 7.73 (d, 2H, J=8.4 Hz); IR (KBr) 3320, 2980, 1745, 1720, 1635, 1520, 1375, 1300, and 1200 cm$^{-1}$. Anal. Calcd. for C$_{16}$H$_{20}$BrNO$_5$: C, 49.75; H, 5.22; N, 3.63; Br, 20.69. Found: C, 49.70; H, 5.15; N, 3.65; Br, 20.90.

Diethyl N-(4-iodobenzoyl)-L-glutamate is prepared from 4-iodobenzoyl chloride and diethyl L-glutamate in 56% yield by the same method. m.p. 105°–106° C.; NMR (CDCl$_3$, 300 MHz) delta 1.26 (t, 3H, J=7.2 Hz), 1.33 (t, 3H, J=7.2 Hz), 2.11–2.60 (m, 4H), 4.14 (q, 2H, J=7.2 Hz), 4.78 (m, 1H), 7.15 (d, 1H, J=7.2 Hz), 7.58 (d, 2H, J=8.4 Hz), 7.83 (d, 2H, J=8.4 Hz).

EXAMPLE 11

Diethyl N-4-(2-pivaloylamino-4-hydroxypyrido[2,3-d]pyrimidine-6-ylethynyl)benzoyl-L-glutamate A mixture of 0.68 g of 2-pivaloylamino-4-hydroxy-6-ethynylpyrido[2,3-d]pyrimidine, 1.20 g of diethyl N-(4-iodobenzoyl)-L-glutamate, 0.35 ml of triethylamine, 0.04 g of palladium chloride, 0.139 of triphenylphosphine, and 0.02 g of cuprous iodide in 75 ml of acetonitrile is heated at reflux under nitrogen for 3.5 hours. The reaction mixture is cooled and the solid collected, triturated with ethyl acetate, and filtered. The solid is recrystallized from ethanol to yield diethyl N-4-(2-pivaloylamino-4-hydroxypyrido[2,3-d]pyrimidin-6-ylethynyl)benzoyl-L-glutamate. m.p. >250° C.; NMR (CDCl$_3$, 300 MHz) delta 1.25 (t, 3H, J=7.20 Hz), 1.33 (t, 3H, J=7.20 Hz), 1.36 (s, 9H), 2.14–2.62 (m, 4H), 4.14 (q, 2H, J=7.20 Hz), 4.27 (q, 2H, J=7.20 Hz) 4.79–4.86 (m, 1H), 7.30 (d, 1H, J=8.40 Hz), 7.63 (d, 2H, J=8.25 Hz), 7.86 (d, 2H, J=8.25 Hz), 8.51 (brs, 1H), 8.64 (d, 1H, J=2.40 Hz), 8.97 (d, 1H, J=2.40 Hz), 12.2 (brs, 1H); IR (KBr) 3330, 3290, 2970, 1730, 1655, 1590, 1530, 1440, 1370, 1260, 1140, 1020, 965, 925, 850, 810, and 760 cm$^{-1}$; $^{13}$C-NMR (CDCl$_3$, 75 MHz) delta 14.3, 27.1, 27.2, 30.7, 40.6, 52.7, 61.1, 62.0, 87.61, 92.71, 115.1, 117.3, 125.9, 127.4, 127.5, 132.0, 133.9, 138.7, 149.6, 157.8, 158.6, 160.5, 166.4 172.1, 173.5, 180.8. Anal. Calcd. for C$_{30}$H$_{33}$N$_5$O$_7$: C, 62.60; H, 5.78; N, 12.35. Found: C, 44.56; H, 3.85; N, 17.30; Br, 24.38.

EXAMPLE 12

2-Pivaloylamino-4-hydroxy-6-(4-tert.-butoxycarbonylphenylethynyl)pyrido[2,3-d]pyrimidine A mixture of 2.0 g of 2-pivaloylamino-4-hydroxy-6-bromopyrido[2,3-d]pyrimidine (prepared according to Example 6), 1.31 g of tert.-butyl 4-ethynylbenzoate, 2.57 ml of triethylamine, 0.11 g of palladium chloride, 0.32 g of triphenylphosphine, and 0.05 g of cuprous iodide in 150 ml of acetonitrile is heated at reflux under nitrogen for 2.5 hours. The reaction mixture is cooled to room temperature and then in an ice bath. The solid is collected and washed with small portions of cold acetonitrile to yield 1.91 g (69%) of 2-pivaloylamino-4-hydroxy-6-(4-tert.-butoxycarbonylphenylethynyl)-pyrido[2,3-d]pyrimidine as a pale yellowish powder, which is sufficiently pure for the next reaction. A small sample of this solid, purified further by chromatography on silica gel using a 5% methanol:methylene chloride mixture as the eluent, had the following constants: m.p. >250° C.; NMR (CDCl$_3$, 300 MHz) delta 1.37 (s, 9H), 1.63 (s, 9H), 7.61 (d, 2H, J=8.50 Hz), 8.02 (d, 2H, J=8.50 Hz), 8.42 (brs, 1H), 8.66 (slightly brs, 9.01 (slightly brs, 1H);IR (KBr) 3200, 2980, 1710, 1670, 1600, 1545, 1440, 1375, 1290, 1140, and 770 cm$^{-1}$.

Alternatively, a mixture of 0.15 g of 2-pivaloylamino-4-hydroxy-6-ethynylpyrido[2,3-d]pyrimidine, 0.16 g of tert.-butyl 4-bromobenzoate, 0.23 ml of triethylamine, 0.01 g of palladium chloride, 0.03 g of triphenylphosphine, and 0.01 g of cuprous iodide in 20 ml of acetonitrile is heated at reflux under nitrogen for 4 hours. Upon cooling, the reaction mixture is filtered to give 0.18 g of a brown solid, which is further purified by radial chromatography using a 5% methanol: methylene chloride solution as the eluent. The major fraction isolated from the plate contained a yellowish solid which was triturated with ethyl acetate to give 0.1 g (40%) of 2-pivaloylamino-4-hydroxy-6-(4-tert.-butoxycarbonylphenylethynyl)pyrido[2,3-d]pyrimidine, constants as above.

EXAMPLE 13

2-Pivaloylamino-4-hydroxy-6-(4-carboxyphenylethynyl)pyrido[2,3-d]pyrimidine

One gram of 2-pivaloylamino-4-hydroxy-6-(4-tert.-butoxycarbonylphenylethynyl)pyrido[2,3-d]pyrimidine is added to 25 ml of nitromethane saturated with hydrogen chloride gas at 0° C. After stirring at 0° C., the reaction mixture is allowed to reach room temperature and stirred for an additional hour. The suspension is diluted with anhydrous ether and suction filtered. The collected solid is washed with ether, methanol, and ether again, and then dried under reduced pressure to give 0.81 g of 2-pivaloylamino-4-hydroxy-6-(4-carboxyphenylethynyl)pyrido[2,3-d]pyrimidine as a yellowish powder: m.p. >250° C.; NMR (CDCl$_3$, 300 MHz) delta 1.25 (s, 9H), 7.72 (d, 2H, J=8.02 Hz), 7.98 (d, 2H, J=8.02 Hz), 8.52 (d, 1H, J=2.01 Hz), 9.01 (d, 1H, J=2.01 Hz); IR (KBr) 3420, 3000, 1725, 1680, 1425, 1405, 1360, 1250, 1130, 1020, and 800 cm$^{-1}$.

Alternatively, 2-amino-4-hydroxy-6-[(4-carboxyphenyl)ethynyl]pyrido[2,3-d]pyrimidine, prepared as described in Example 5, is heated in refluxing pivalic anhydride according to the procedure of Example 6 to yield 2-pivaloylamino-4-hydroxy-6-[(4-carboxyphenyl)ethynyl]pyrido[2,3-d]pyrimidine.

EXAMPLE 14

Diethyl N-4-(2-pivaloylamino-4-hydroxypyrido[2,3-d]pyrimidine-6-ylethynyl)benzoyl-L-glutamate To a solution of 0.09 g of 2-pivaloylamino-4-hydroxy-6-(4-carboxyphenylethynyl)pyrido[2,3-d]pyrimidine and 0.07 ml of N-methylmorpholine in 5 ml of dry N-methylpyrrolidone is added 0.09 g of phenyl N-phenylphosphoramidochloridate. After stirring the reaction mixture at room temperature under a nitrogen atmosphere for 20 minutes, 0.08 g of diethyl L-glutamate hydrochloride is added and the mixture stirred for another 24 hours. The solvent is removed by distillation under reduced pressure and the residue is partitioned between chloroform and water. The organic phase is dried over anhydrous sodium sulfate and concentrated under reduced pressure. The residue is subjected to repeated chromatography on silica gel using a 2% methanol:methylene chloride mixture as the eluent. The major fraction isolated contained 0.05 g (38%) of diethyl N-4-(2-pivaloylamino-4-hydroxypyrido[2,3-d]pyrimidine-6-ylethynyl)benzoyl-L-glutamate which has a m.p. >250° C., constants as reported in Examples 8 and 11.

EXAMPLE 15

Diethyl N-(4-[2-(2-pivaloylamino-4-hydroxy-5,6,7,8-tetrahydropyrido[2,3-d]pyrimidin-6-yl)ethyl]benzoyl)-L-glutamate A mixture of 0.59 g of diethyl N-[4-(2-pivaloylamino-4-hydroxypyrido[2,3-d]pyrimidin-6-ylethynyl)benzoyl]-L-glutamate and 1.5 g of 5% palladium on charcoal in 30 ml of trifluoroacetic acid is hydrogenated at 53 psi at room temperature for 24.5 hours. The reaction mixture is diluted with methylene chloride and filtered through Celite. The solvent is removed under reduced pressure. The residue is redissolved in methylene chloride and extracted with a saturated sodium bicarbonate solution and dried over anhydrous sodium sulfate. The solvent is removed under reduced pressure and the residue chromatographed on silica gel using a 4% methanol:methylene chloride mixture as the eluent. Evaporation of the eluate yields 0.60 g (100%) of diethyl N-(4-[2-(2-pivaloylamino-4-hydroxy-5,6,7,8-tetrahydropyrido[2,3-d]pyrimidin-6-yl)ethyl]benzoyl)-L-glutamate as a white solid: m.p. >250° C.; NMR (CDCl$_3$, 300 MHz) delta 1.22 (t, 3H, J=7.20 Hz), 1.29 (s, 9H), 1.30 (t, 3H, J=7.20 Hz), 1.61–3.35 (m, 13 H), 4.11 (q, 2H, J=7.20 Hz), 4.23 (q, 2H, J=7.20 Hz), 4.77–4.84 (m, 1H), 5.15 (brs, 1H), 7.17 (d, 1H, J=7.50 Hz), 7.23 (d, 2H, J=8.10 Hz), 8.56 (brs, 1H); IR (KBr) 3400, 3280, 2980, 1735, 1630, 1570, 1460, 1390, 1350, 1310, 1200, 1155, 1025, 930, and 800 cm$^{-1}$. Anal. Calcd. for C$_{30}$H$_{37}$N$_5$O$_7$: C, 61.73; H, 7.08; N, 12.00. Found: C, 44.56; H, 3.85; N, 17.30; Br, 24.38.

EXAMPLE 16

N-(4-[2-(2-amino-4-hydroxy-5,6,7,8-tetrahydropyrido[2,3-d]pyrimidin-6-yl)ethyl]benzoyl)-L-glutamatic acid A solution containing 0.53 g of diethyl N-(4-[2-(2-pivaloylamino-4-hydroxy-5,6,7,8-tetrahydropyrido[2,3-d]pyrimidin-6-yl)ethyl]benzoyl)-L-glutamate, 3 ml of a 1 sodium hydroxide solution in 50 ml of methanol is stirred at room temperature for 70 hours. The mixture is acidified with acetic acid and the solid which forms is filtered, washed with methanol, and dried under reduced pressure to give 0.20 g (50%) of the known N-(4-[2-(2-amino-4-hydroxy-5,6,7,8-tetrahydropyrido[2,3-d]pyrimidin-6-yl)ethyl]benzoyl)-L-glutamatic acid.

What is claimed is:

1. In the process of preparing a compound of the formula:

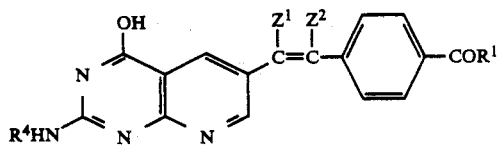

wherein
R$^1$ is —NHCH(COOR$_2$)CH$_2$CH$_2$COOR$^2$ or OR$^2$;
R$^2$ is hydrogen or a carboxylic acid protecting group;
R$^4$ is hydrogen or an amino protecting group;
Z$^1$ when taken independently of Z$^2$ is hydrogen; and
Z$^2$ when taken independently of Z$^1$ is hydrogen, methyl or ethyl; or
Z$^1$ and Z$^2$ when taken together are a carbon-carbon bond;
the step of allowing an unsaturated compound to react with a haloaromatic compound in the presence of a palladium catalyst, said unsaturated compound and said haloaromatic compound being selected such that said haloaromatic compound is (i) a pyridine of the formula:

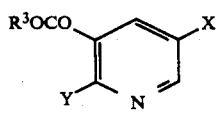

wherein
Y is amino or a nucleofuge;
X is bromo or iodo; and
R$^3$ is alkyl of 1 to 4 carbon atoms; or
(ii) a fused pyridine of the formula:

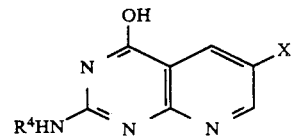

wherein
R$^4$ is as defined above;
X is bromo or iodo; and
said unsaturated compound is of the formula:

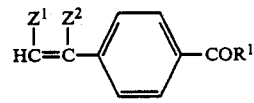

wherein
Z$^1$, Z$^2$, R$^1$, and R$^2$ are as defined above.

2. The process according to claim 1 wherein the haloaromatic compound is a fused pyridine of the formula:

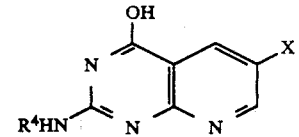

wherein
R$^4$ is hydrogen or an amino protecting group and
X is bromo or iodo; and
said palladium catalyst is generated from a triarylphosphine, a palladium halide salt, and a cuprous halide salt.

3. The process according to claim 2 in which R$^1$ is OR$^2$, and R$^2$ contains a chiral center and is in one chiral form substantially free of the other.

4. The process according to claim 2 wherein R$^1$ is alkoxy of 1 to 10 carbon atoms.

5. The process according to claim 4 wherein R$^1$ is tert.-butoxy.

6. The process according to claim 4 wherein R$^4$ is alkanoyl of 2 to 10 carbon atoms inclusive of the carbonyl carbon atom.

7. The process according to claim 6 wherein R$^4$ is pivaloyl.

8. The process according to claim 2 in which a 2-alkamido-4-hydroxy-6-iodopyridopyrimidine is allowed to react with a dialkyl ester of N-(4-ethynylbenzoyl)-L-glutamic acid.

9. The process according to claim 2 in which a 2-alkamido-4-hydroxy-6-bromopyridopyrimidine is allowed to react with a dialkyl ester of N-(4-ethynylbenzoyl)-L-glutamic acid.

10. The process according to claim 2 wherein the reaction is conducted in acetonitrile as a solvent.

11. The process according to claim 1 wherein the haloaromatic compound is a pyridine of the formula:

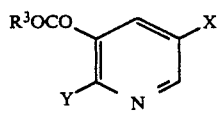

wherein
Y is amino or a nucleofuge;
X is bromo or iodo; and
$R^3$ is alkyl of 1 to 4 carbon atoms;
said unsaturated compound is of the formula:

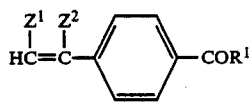

wherein
$Z^1$ when taken independently of $Z^2$ is hydrogen;
$Z^2$ when taken independently of $Z^1$ is hydrogen, methyl or ethyl; or
$Z^1$ and $Z^2$ when taken together are a carbon-carbon bond;
$R^1$ is $-NHCH(COOR^2)CH_2CH_2COOR^2$ or $OR^2$; and
$R^2$ is a carboxylic acid protecting group; and
said palladium catalyst is generated from a triarylphosphine, a palladium halide salt, and a cuprous halide salt.

12. A process according to claim 11 wherein $R^1$ is alkoxy of 1 to 10 carbon atoms and Y is chloro, bromo, iodo, an aryl or alkylsulfinyl or -sulfonyl group of up to 10 carbon atoms, an arylthio or alkylthio group of up to 10 carbon atoms, mercapto, or alkoxy of up to 10 carbon atoms.

13. A process according to claim 12 wherein $R^3$ is methyl and Y is chloro.

14. The process according to claim 11 in which $R^1$ is $OR^2$, and $R^2$ contains a chiral center and is in one chiral form substanstantially free of the other.

15. The process according to claim 11 wherein $R^1$ is alkoxy of 1 to 10 carbon atoms.

16. The process according to claim 15 wherein $R^1$ is tert.-butoxy.

17. The process which comprises
(1) allowing a haloaromatic compound of the formula:

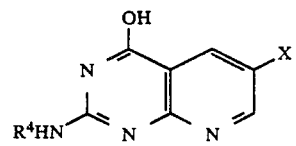

wherein
$R^4$ is hydrogen or an amino protecting group and X is bromo or iodo,
to reach with an unsaturated compound of the formula:

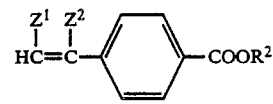

wherein
$Z^1$ when taken independently of $Z^2$ is hydrogen;
$Z^2$ when taken independently of $Z^1$ is hydrogen, or
$Z^1$ and $Z^2$ when taken together are a carbon-carbon bond and
$R^2$ is a carboxylic acid protecting group, in the presence of a palladium catalyst, to yield an unsaturated compound of the formula:

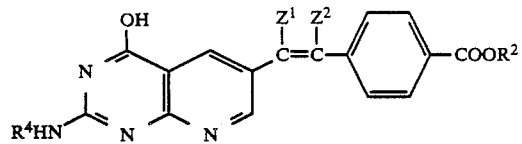

and
(2) catalytically hydrogenating said unsaturated compound to yield a protected derivative of 2-amino-4-hydroxy-5,6,7,8-tetrahydro-6-[2-(4-carboxyphenyl)ethyl]pyrido[2,3-d]pyrimidine of the formula:

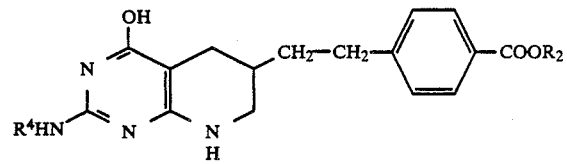

in which $R^2$, $R^3$ and $Z^2$ are as defined above.

18. The process according to claim 17 which comprises removing said protecting groups to yield 2-amino-4-hydroxy-5,6,7,8-tetrahydro-6-[2-(4-carboxyphenyl)ethyl]pyrido[2,3-d]pyrimidine.

19. 2-Amino-4-hydroxy-5,6,7,8-tetrahydro-6-[2-(4-carboxyphenyl)ethyl]pyrido[2,3-d]pyrimidine.

* * * * *